US005725526A

United States Patent [19]
Allard et al.

[11] Patent Number: 5,725,526
[45] Date of Patent: Mar. 10, 1998

[54] TRANSPORT CARRIAGE FOR AN EXTERNAL FIXATOR

[75] Inventors: Randall N. Allard, Plymouth; Kenneth S. Jackson, Warsaw; John E. Meyers, Columbia City; James F. Hanneken, North Manchester, all of Ind.; Ronald Lakatos, Columbus, Ohio

[73] Assignee: Zimmer, Inc., Warsaw, Ind.

[21] Appl. No.: 623,093

[22] Filed: Mar. 28, 1996

Related U.S. Application Data

[63] Continuation-in-part of Ser. No. 562,724, Nov. 27, 1995.

[51] Int. Cl.$^6$ ............................... A61B 17/60
[52] U.S. Cl. ............... 606/57; 606/54; 606/59; 606/105
[58] Field of Search .................... 606/54, 57, 58, 606/59, 105

[56] References Cited

U.S. PATENT DOCUMENTS

| 4,356,571 | 11/1982 | Esper et al. ................... 3/1 |
| 4,502,473 | 3/1985 | Harris et al. ............... 128/92 A |
| 4,848,368 | 7/1989 | Kronner ..................... 128/92 Z |
| 4,893,618 | 1/1990 | Herzberg ........................ 606/54 |
| 4,902,297 | 2/1990 | Devanathan ..................... 623/16 |
| 4,978,348 | 12/1990 | Ilizarov ........................... 606/57 |
| 4,978,350 | 12/1990 | Wagenknecht ................... 606/72 |
| 5,019,077 | 5/1991 | Bastiani et al. ................ 606/54 |
| 5,064,439 | 11/1991 | Chang et al. ................... 623/66 |
| 5,152,687 | 10/1992 | Amino ........................... 433/173 |
| 5,163,962 | 11/1992 | Salzstein et al. ............... 623/23 |
| 5,181,930 | 1/1993 | Dumbleton et al. ............ 623/23 |
| 5,192,330 | 3/1993 | Chang et al. ................... 623/22 |
| 5,207,676 | 5/1993 | Canadell et al. ............... 606/54 |
| 5,275,599 | 1/1994 | Zbikowski et al. ............. 606/54 |
| 5,314,426 | 5/1994 | Pohl et al. ..................... 606/58 |
| 5,397,358 | 3/1995 | Wenner et al. ................. 623/16 |
| 5,397,365 | 3/1995 | Trentacosta .................... 623/18 |
| 5,439,465 | 8/1995 | Tumibay ....................... 606/105 |
| 5,443,464 | 8/1995 | Russell et al. .................. 606/54 |
| 5,443,513 | 8/1995 | Moumene et al. .............. 623/16 |
| 5,458,599 | 10/1995 | Adobbati ....................... 606/56 |

FOREIGN PATENT DOCUMENTS

| 0 159 007 A2 | 10/1985 | European Pat. Off. . |
| 0 517 939 A1 | 12/1992 | European Pat. Off. . |
| WO 95/24870 | 9/1995 | WIPO ................. A61B 17/58 |

Primary Examiner—Michael Buiz
Assistant Examiner—Daphna Shai
Attorney, Agent, or Firm—Todd A. Dawson

[57] ABSTRACT

The transport carrier of this invention is configured for use with an external fixator having a hexagonal rod. The carrier includes a threaded sleeve which accommodates the hexagonal rod of the fixator. A compressible ball collet and retaining nut are carried by the sleeve and serve to lock the sleeve into position on the rod in a known manner. A clamp is carried by the sleeve and rotationally fixed relative to the rod by a key and key way, yet may shift along the sleeve. The clamp is configured to connect to one or more bone pins using a ball collet and retaining nut to fix the clamp to the pin. The bone pins connect to a bone fragment such that as the clamp shifts along the sleeve, the bone fragment is transported between two portions of a bone. An internally threaded sleeve is carried by the externally threaded sleeve and engages the clamp. Upon rotation of the internally threaded sleeve, the clamp and externally threaded sleeve move longitudinally along the sleeve.

8 Claims, 2 Drawing Sheets

1

TRANSPORT CARRIAGE FOR AN EXTERNAL FIXATOR

RELATED APPLICATIONS

This application is a continuation-in-part of co-pending U.S. patent application 08/562,724 filed Nov. 27, 1995.

FIELD OF THE INVENTION

This invention relates to an orthopaedic fixator and has specific relevance to a transport carriage for use with an external fixator for transporting a bone fragment between two portions of the bone.

SUMMARY OF THE INVENTION

Transport carriers are well known in the field of orthopaedics. Typically, the transport carrier is associated with an external fixator and is engaged to slowly move a bone fragment, over time, away from another portion of a bone to assist in the healing process. One example of such use could be a leg lengthening procedure wherein the transport carriage would be utilized to shift a bone fragment which has been created by forming two transverse cuts in the bone. The external fixator would be connected to the proximal and distal portions of the femur through bone pins. The transport carriage could be connected to a bone fragment for proper positioning of the fragment and to transport the fragment to close the bone defect. Once the gap in the bone is closed, the femur is restored to its original length and the bone can properly heal.

The transport carrier of this invention is configured for use with an external fixator having a hexagonal rod. The carrier includes a threaded sleeve which accommodates the hexagonal rod of the fixator. A compressible ball collet and retaining nut are carried by the sleeve and serve to lock the sleeve into position on the rod in a known manner. A clamp is carried by the sleeve and rotationally fixed relative to the rod by a key and key way, yet may shift along the sleeve. The clamp is configured to connect to one or more bone pins using a ball collet and retaining nut to fix the clamp to the pin. The bone pins connect to a bone fragment such that as the clamp shifts along the sleeve, the bone fragment is transported between two portions of a bone. An internally threaded sleeve is carried by the externally threaded sleeve and engages the clamp. Upon rotation of the internally threaded sleeve, the clamp and externally threaded sleeve move longitudinally along the sleeve.

Accordingly, it is an object of the invention to provide for a transport carrier configured for use with an external fixator having a hexagonal rod.

Another object of the invention is to provide a transport carrier for a bone fragment wherein a clamp is held rotationally fixed relative to a sleeve yet can shift longitudinally along the rod.

Another object of the invention is to provide for a novel transport carrier for a bone fragment.

Other objects of the invention will become apparent upon a reading of the following description taken with the accompanying drawings.

DESCRIPTION OF THE PREFERRED EMBODIMENT

The preferred embodiment herein described is not intended to be exhaustive or to limit the application to the precise form disclosed. Rather, it is chosen and described in order to explain the invention to those skilled in the art so that they may utilize its teachings.

Figure 1:
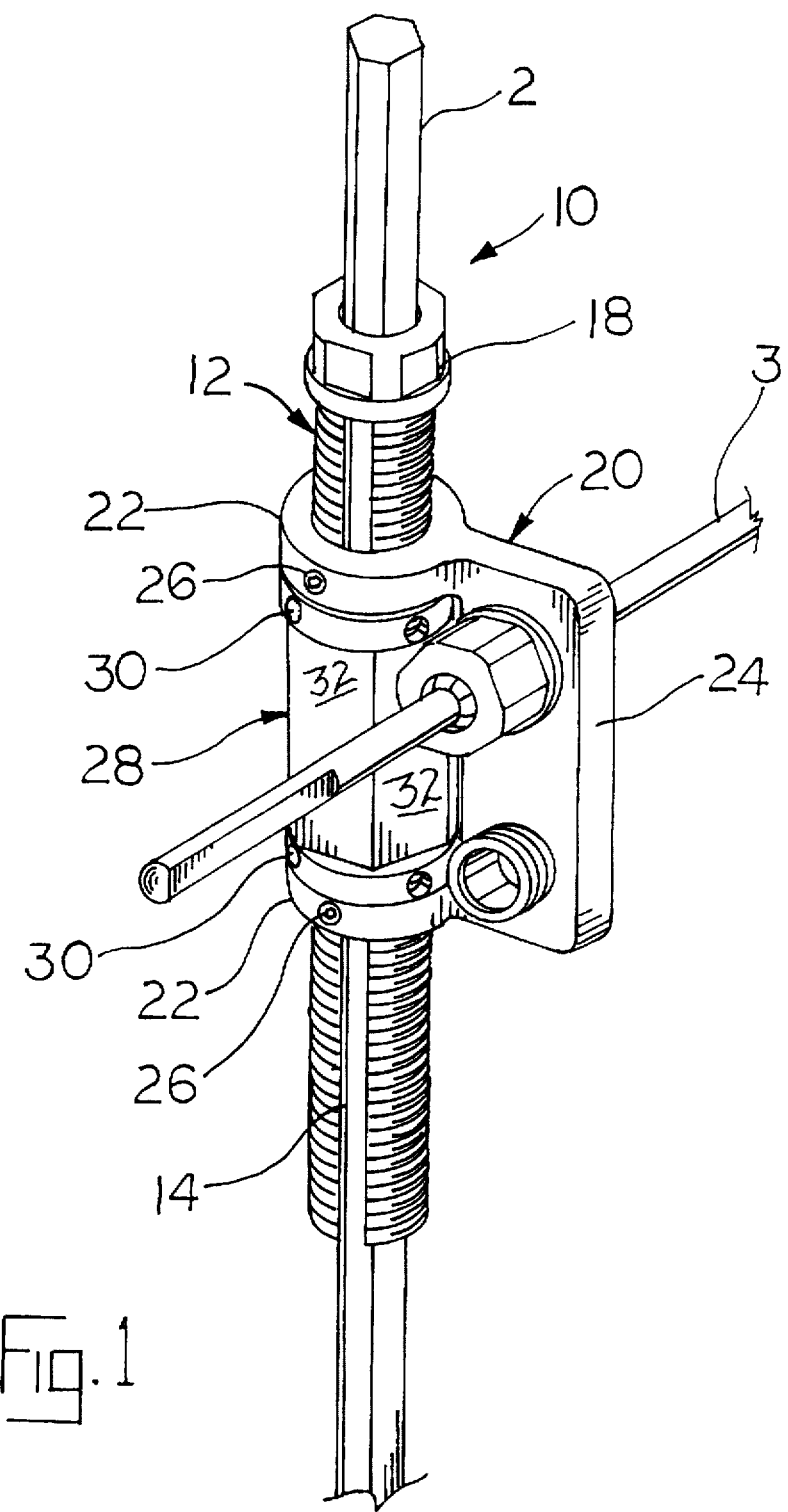
FIG. 1 is a perspective view of the transport carrier of the invention connected to a hexagonal rod (only partially shown) and a bone pin (only partially shown).
Figure 2:
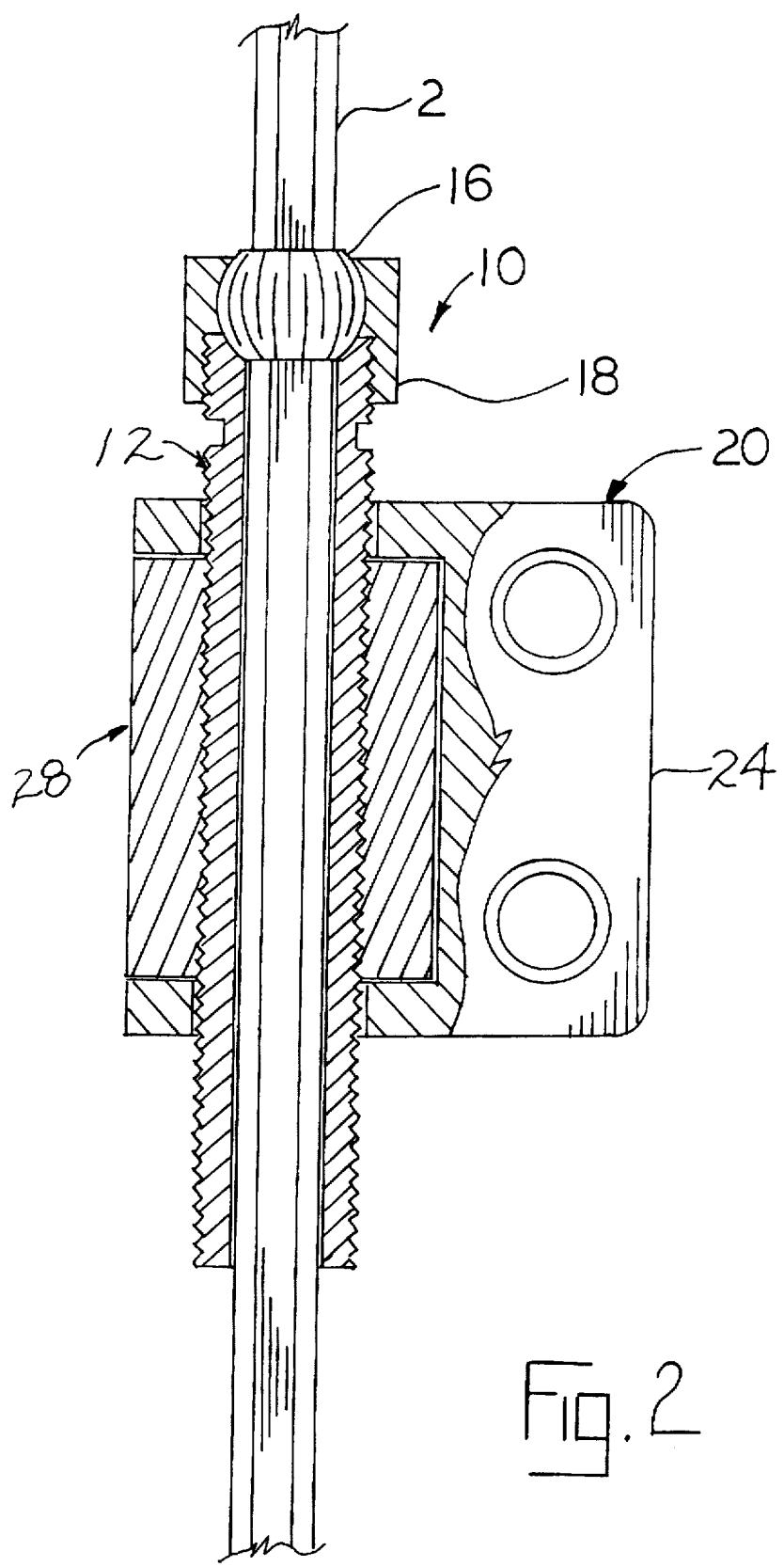
FIG. 2 is a longitudinal sectional view of FIG. 1.

FIGS. 1 and 2 illustrate the transport carrier 10 of the invention connected to a hexagonal rod 2 (partially shown) of an external fixator as used in orthopaedic surgery. A more complete description of an external fixator having a hexagonal rod may be had by a reading of U.S. Pat. No. 5,443,464 issued Aug. 22, 1995, and incorporated herein by reference. Transport carrier 10 includes an elongate externally threaded sleeve 12 having a key way 14 formed along the longitudinal dimension of the sleeve. One end of sleeve 12 is adapted to receive a ball collet 16 and retaining nut 18. As fully explained in the '464 patent, ball collet 16 and nut 18 combine to compress the ball collet about the rod 2 as the nut is tightened onto sleeve 12. A clamp 20 having a pair of spaced apart rings 22 integrally formed with a base 24 is carried by the sleeve 12 passing through the interior of the rings as illustrated. A set screw or key 26 extend through each ring 22 and into key way 14 on sleeve 12 to maintain clamp 20 rotationally fixed relative to the sleeve. As illustrated clap 20 is configured to accommodate one or more bone pins 3. Each bone pin 3 (only one shown) is fixed to clamp 20 by a ball collet and retaining nut as fully described in the '464 patent, previously incorporated. An internally threaded sleeve 28 is threadibly carried on sleeve 12 between rings 22 of damp 20 as shown. A series of threaded openings 30 are formed through sleeve 28 to accommodate a lock screw (not shown) therein. The exterior periphery of sleeve 28 has a plurality of contiguous flats 32 formed therein to accommodate a standard open end wrench (not shown).

In use, the external fixator (not shown) is connected through pins or wires to a long bone on each side of a fracture in a known manner with the transport carrier oriented on the external fixator rod 2. To make a large adjustment of the position of the transport carrier, the user loosens retaining nut 18 which allows the transport carrier to slide along rod 2 to the desired position. After the proper position is located, nut 18 is tightened onto sleeve 12 thus compressing ball collet 16 onto rod 2 in clamping engagement. Next the surgeon inserts one or more bone pins into a bone fragment (not shown) such that the pins extend through the openings in base 24 of clamp 20. The pins are secured to the clamp by a ball collet being compressed about the pin by a retaining nut as in the prior art. At this point the sleeve 12 is fixed to the external fixator rod and the damp is rotationally fixed to the sleeve through the interaction of keys 26 and key way 14. To shift clamp 20 along sleeve 12, internally threaded sleeve 28 is rotated relative to sleeve 12 through use of an open end wrench (not shown). As sleeve 28 rotates relative to sleeve 12, it travels longitudinally along sleeve 12 through interaction of the external and internal threads. As sleeve 28 travels along sleeve 12, sleeve 28 contacts one ring 22 of clamp 20 to shift the clamp longitudinally along sleeve 12. Once the clamp (with the bone fragment attached thereto) is properly positioned, a set screw (not shown) may be threaded into one of the threaded openings 30 in sleeve 28 until a portion of the screw extends into key way 14. If additional movement is desked, the set screw is removed from the key way to permit sleeve 28 to rotate relative to sleeve 12.

Therefore, to make a macro adjustment to the position of clamp 20, the surgeon loosens retaining nut 18 and slides the sleeve 12 along the rod 2. To make more micro adjustments to the position of the clamp, the surgeon can rotate sleeve 28 relative to sleeve 12 in the manner described.

It should be understood that while a specific key way is described and illustrated, the rod could be formed in a non-circular profile having at least one flat side. In that case, the key 26 would contact the flat side of the rod to prevent the rotation of the transport carrier relative to the rod.

It should be further understood that the invention should not be limited to the precise details above but may modified within the teachings of the appended claims.

We claim:

1. A transport carrier for connection to an external fixation device for use in orthopaedic procedures, the carrier includes a first sleeve being externally threaded, means carried by said first sleeve configured to lock said first sleeve to said external fixation device, a clamp means carried by said first sleeve configured to engage at least one bone pin, second sleeve means being internally threaded and in threaded engagement with said first sleeve and rotatable relative thereto to shift said clamp means along said first sleeve, and means to selectively rotationally fix the second sleeve to the first sleeve.

2. The transport carrier of claim 1 further wherein said clamp means includes a pair of spaced apart rings, wherein the first sleeve extends through an interior of said rings, said second sleeve being positioned between said rings on said first sleeve.

3. The transport carrier of claim 1 further including means to rotationally fix the clamp means relative to the first sleeve.

4. A transport carrier for connection to a non-circular external fixation rod, said carrier including an externally threaded sleeve, a locking device for selectively locking the externally threaded sleeve to said external fixation rod, a clamp having a body and a pair of aligned rings being carried by the externally threaded sleeve such that the externally threaded sleeve extends freely through an interior opening of each of the rings, the clamp including means for accommodating at least one bone pin in clamping engagement relative to the clamp, an internally threaded sleeve being carried by the externally threaded sleeve and in threaded engagement therewith such that as the internally threaded sleeve is rotated relative to the externally threaded sleeve, the internally threaded sleeve shifts longitudinally along the externally threaded sleeve, the internally threaded sleeve being carried on the externally threaded sleeve between the rings of the clamp, and means for selectively rotationally fixing said internally threaded sleeve relative th the externally threaded sleeve.

5. The transport carrier of claim 4 further including means for rotationally fixing the clamp relative to the externally threaded sleeve.

6. A transport carrier for connection to an external fixation device for use in orthopaedic procedures, the carrier includes a first sleeve being externally threaded, means carried by said first sleeve configured to lock said first sleeve to said external fixation device, a clamp means carried by said first sleeve configured to engage at least one bone pin, second sleeve means being internally threaded and in threaded engagement with said first sleeve and rotatable relative thereto to shift said clamp means along said first sleeve, wherein said clamp means includes a pair of spaced apart rings, wherein the first sleeve extends through an interior of said rings, said second sleeve being positioned between said rings on said first sleeve.

7. The transport carrier of claim 6 further including means to rotationally fix the clamp means relative to the first sleeve.

8. The transport carrier of claim 6 further including means to selectively rotationally fix the second sleeve to the first sleeve.

* * * * *